United States Patent
Adamson et al.

(10) Patent No.: US 11,376,445 B1
(45) Date of Patent: Jul. 5, 2022

(54) SYSTEMS AND METHODS FOR SINGLE ISOCENTER RADIOTHERAPY OF MULTIPLE TARGETS

(71) Applicant: Duke University, Durham, NC (US)

(72) Inventors: Justus Adamson, Durham, NC (US); William Giles, Durham, NC (US); Obed Laryea, Durham, NC (US); Fang-Fang Yin, Durham, NC (US)

(73) Assignee: Duke University, Durham, NC (US)

( * ) Notice: Subject to any disclaimer, the term of this patent is extended or adjusted under 35 U.S.C. 154(b) by 177 days.

(21) Appl. No.: 16/819,855

(22) Filed: Mar. 16, 2020

Related U.S. Application Data

(60) Provisional application No. 62/818,157, filed on Mar. 14, 2019.

(51) Int. Cl.
*A61N 5/10* (2006.01)

(52) U.S. Cl.
CPC ......... *A61N 5/1031* (2013.01); *A61N 5/1036* (2013.01); *A61N 5/1047* (2013.01); *A61N 5/1069* (2013.01); *A61N 2005/1072* (2013.01)

(58) Field of Classification Search
CPC .. A61B 6/06; A61B 6/40; A61B 6/405; A61B 34/10; A61B 34/20; A61B 2034/107; A61N 5/10; A61N 5/103; A61N 5/1031; A61N 5/1036; A61N 5/1042; A61N 5/1045; A61N 5/1047; A61N 5/1048; A61N 5/1064; A61N 5/1065; A61N 5/1071; A61N 5/10745; A61N 2005/1032; G21K 1/02; G21K 1/04; G21K 1/046; H01J 2237/04; H01J 2237/045; H01J 2237/0455; H01J 2237/15; H01J 2237/1501; H01J 2237/1502; H05G 1/26; H05G 1/30
See application file for complete search history.

(56) References Cited

U.S. PATENT DOCUMENTS

| | | | |
|---|---|---|---|
| 6,813,336 B1 * | 11/2004 | Siochi | A61N 5/1047 378/147 |
| 9,061,142 B2 | 6/2015 | Vilsmeier | |
| 2010/0020931 A1 * | 1/2010 | Otto | A61N 5/1038 378/65 |
| 2011/0091014 A1 * | 4/2011 | Siljamaki | A61N 5/1031 378/65 |

(Continued)

OTHER PUBLICATIONS

Adamson, J., et al. "Delivered Dose Distribution Visualized Directly With Onboard kV-CBCT: Proof of Principle." International Journal of Radiation Oncology* Biology* Physics 103.5 (2019): 1271-1279.

(Continued)

*Primary Examiner* — Anastasia Midkiff
(74) *Attorney, Agent, or Firm* — Quarles & Brady, LLP

(57) ABSTRACT

Systems and methods are provided for single isocenter radiotherapy of multiple targets. Conformal arc information may be used in a Conformal Arc Informed Volumetric Modulated Arc Therapy (CAVMAT) method that includes single isocenter radiotherapy of multiple targets where conformal multi-leaf collimator (MLC) trajectories may be used as the starting point for limited inverse optimization. Single isocenter radiotherapy of multiple targets may provide flexibility with less complex MLC trajectories, and fully block between targets with the MLC.

18 Claims, 6 Drawing Sheets

(56) References Cited

U.S. PATENT DOCUMENTS

| | | | | |
|---|---|---|---|---|
| 2013/0142310 | A1* | 6/2013 | Fahimian | A61N 5/103 378/65 |
| 2014/0330064 | A1* | 11/2014 | Xing | A61N 5/1031 600/1 |
| 2014/0330065 | A1* | 11/2014 | Vilsmeier | A61N 5/103 600/1 |
| 2018/0154179 | A1* | 6/2018 | Ollila | A61N 5/1065 |

OTHER PUBLICATIONS

Alongi, F., et al. (2019). First experience and clinical results using a new non-coplanar mono-isocenter technique (HyperArcTM) for Linac-based VMAT radiosurgery in brain metastases. Journal of Cancer Research and Clinical Oncology, 145(1), 193-200. https://doi.org/10.1007/s00432-018-2781-7.

Amsbaugh, M. J. et al. (2016). A Dose-Volume Response Model for Brain Metastases Treated With Frameless Single-Fraction Robotic Radiosurgery. Technology in Cancer Research & Treatment, 8(4), 1-13. https://doi.org/10.1177/1533034616685025.

Audet, C. et al. Evaluation of volumetric modulated arc therapy for cranial radiosurgery using multiple noncoplanar arcs Med Phys, 38 (2011), pp. 5863-5872.

Ballangrud, A. et al. (2018). Institutional experience with SRS VMAT planning for multiple cranial metastases. Journal of Applied Clinical Medical Physics, 19(2), 176-183. https://doi.org/10.1002/acm2.12284.

Brown, P. D., et al. (2016). Effect of radiosurgery alone vs radiosurgery with whole brain radiation therapy on cognitive function in patients with 1 to 3 brain metastases a randomized clinical trial. JAMA—Journal of the American Medical Association, 316(4), 401-409. https://doi.org/10.1001/jama.2016.9839.

Chyu, K-Y, et al. "Vaccine against arteriosclerosis: an update." Therapeutic advances in vaccines 5.2 (2017): 39-47.

Clark, G.M. et al. Feasibility of single-isocenter volumetric modulated arc radiosurgery for treatment of multiple brain metastases Int J Radiat Oncol Biol Phys, 76 (2010), pp. 296-302.

Clark, G.M. et al. Plan quality and treatment planning technique for single isocenter cranial radiosurgery with volumetric modulated arc therapy Pract Radiat Oncol, 2 (2012), pp. 306-313.

Das, I. J., et al. (2008). Accelerator beam data commissioning equipment and procedures: Report of the TG-106 of the Therapy Physics Committee of the AAPM. Medical Physics, 35(9), 4186-4215. https://doi.org/10.1118/1.2969070.

Das, I. J., et al. (2008). Small fields: Nonequilibrium radiation dosimetry. Medical Physics, 35(1), 206-215. https://doi.org/10.1118/1.2815356.

Ding, M. et al. Comparative dosimetric study of three-dimensional conformal. Dynamic conformal arc, and intensity modulated radiotherapy for brain treatment using Novalis system Int J Radiat Oncol Biol Phys, 66 (2006), pp. S82-S86.

Farrukh, S., et al. (2017). Penumbral Dose Characteristics of Physical and Virtual Wedge Profiles. International Journal of Medical Physics, Clinical Engineering and Radiation Oncology, 06(02), 216-224. https://doi.org/10.4236/jmpcero.2017.62020.

Faught, A. M., et al. "Re-examining TG-142 recommendations in light of modern techniques for linear accelerator based radiosurgery." Medical physics 43.10 (2016): 5437-5441.

Fraass B, et al. American association of physicists in medicine radiation therapy committee task group 53: Quality assurance for clinical radiotherapy treatment planning. Med Phys. 1998;25(10):1773-1829. doi:10.1118/1.598373.

Fusella, M., et al. (2018). Efficiently train and validate a RapidPlan model through APQM scoring. Medical Physics, 45(6), 2611-2619. https://doi.org/10.1002/mp.12896.

Gevaert, T., et al. (2016). Evaluation of a dedicated brain metastases treatment planning optimization for radiosurgery: A new treatment paradigm? Radiation Oncology, 11(1), 1-7. https://doi.org/10.1186/s13014-016-0593-y.

Graves, M. N., et al. (2001). Calibration and quality assurance for rounded leaf-end MLC systems. Medical Physics, 28(11), 2227-2233. https://doi.org/10.1118/1.1413517.

Gregucci, F., et al. "Linac-based radiosurgery or fractionated stereotactic radiotherapy with flattening filter-free volumetric modulated arc therapy in elderly patients." Strahlentherapie und Onkologie 195.3 (2019): 218-225.

Hirashima, H., et al. (2018). Monitoring of mechanical errors and their dosimetric impact throughout the course of non-coplanar continuous volumetric-modulated arc therapy. Radiation Oncology, 13(1). https://doi.org/10.1186/s13014-018-0972-7.

Huang, Y., et al. (2014). Radiosurgery of multiple brain metastases with single-isocenter dynamic conformal arcs (SIDCA). Radiotherapy and Oncology, vol. 112, pp. 128-132. https://doi.org/10.1016/j.radonc.2014.05.009.

Kang, J., et al. (2010). A method for optimizing LINAC treatment geometry for volumetric modulated arc therapy of multiple brain metastases. Medical Physics, 37(8), 4146-4154. https://doi.org/10.1118/1.3455286.

Klein, E. E., et al. (2009). Task group 142 report: Quality assurance of medical acceleratorsa. Medical Physics, 36(9), 4197-4212. https://doi.org/10.1118/1.3190392.

Lau, Steven KM, et al. "Single-isocenter frameless volumetric modulated arc radiosurgery for multiple intracranial metastases." Neurosurgery 77.2 (2015): 233-240.

Lawrence, Y. R., et al. (2010). Radiation Dose-Volume Effects in the Brain. International Journal of Radiation Oncology Biology Physics,76(3SUPPL.),20-27. https://doi.org/10.1016/j.ijrobp.2009.02.091.

Lim, S. , et al. (2016), SU-G-BRC-05: Conundrum for VMAT Cranial Multiple Lesions Treated with HD120 MLC. Med. Phys., 43: 3628-3628. doi:10.1118/1.4956895.

Limon D, et al. Single fraction stereotactic radiosurgery for multiple brain metastases. Adv Radiat Oncol. 2017;2 (4):555-563. doi:10.1016/j.adro.2017.09.002.

Lin, C. Y., et al. (2018). A simple method for determining dosimetric leaf gap with cross-field dose width for rounded leaf-end multileaf collimator systems. Radiation Oncology (London, England), 13(1), 222. https://doi.org/10.1186/s13014-018-1164-1.

Liu, H., et al. (2018). Comparison of the progressive resolution optimizer and photon optimizer in VMAT optimization for stereotactic treatments. Journal of Applied Clinical Medical Physics, 19(4), 155-162. https://doi.org/10.1002/acm2.12355.

Macdonald RL, et al. "Intra-arc binary collimation algorithm for the optimization of stereotactic radiotherapy treatment of multiple metastases with multiple prescriptions." Medical physics 45.12 (2018): 5597-5607.

Macdonald RL, et al. Dynamic collimator trajectory algorithm for multiple metastases dynamic conformal arc treatment planning. Med Phys. 2018;45(1):5-17. doi:10.1002/mp.12648.

Masi, L., et al. (2013). Impact of plan parameters on the dosimetric accuracy of volumetric modulated arc therapy. Medical Physics, 40(7). https://doi.org/10.1118/1.4810969.

Mcniven, A.L., et al. (2010), A new metric for assessing IMRT modulation complexity and plan deliverability. Med. Phys., 37: 505-515. doi:10.1118/1.3276775.

Minniti, G., et al. (2011). Stereotactic radiosurgery for brain metastases: Analysis of outcome and risk of brain radionecrosis. Radiation Oncology, 6(1), 48. https://doi.org/10.1186/1748-717X-6-48.

Minniti, G., et al. (2014). Fractionated stereotactic radiosurgery for patients with brain metastases. Journal of Neuro-Oncology, 117(2), 295-301. https://doi.org/10.1007/s11060-014-1388-3.

Morrison, J., et al. "Is a single isocenter sufficient for volumetric modulated arc therapy radiosurgery when multiple intracranial metastases are spatially dispersed?." Medical Dosimetry 41.4 (2016): 285-289.

Nelder, J.A. et al, A Simplex Method for Function Minimization, The Computer Journal, vol. 7, Issue 4, Jan. 1965, pp. 308-313, https://doi.org/10.1093/comjnl/7.4.308.

Ohira, S., et al. "HyperArc VMAT planning for single and multiple brain metastases stereotactic radiosurgery: a new treatment planning approach." Radiation Oncology 13.1 (2018): 13.

(56) References Cited

OTHER PUBLICATIONS

Okumura, T., et al. (2016). Verification of Mechanical and Dosimetric Accuracy for Head and Neck Volumetric Modulated Arc Therapy With Jaw Tracking. International Journal of Radiation Oncology*Biology*Physics, 96(2), E638. https://doi.org/10.1016/j.ijrobp.2016.06.2226.

Pant, K., et al. "Comprehensive Radiation and Imaging Isocenter Verification Using NIPAM kV-CBCT Dosimetry." Medical Physics 47.3 (2020): 927-936.

Park, J. M., et al. (2015). The effect of MLC speed and acceleration on the plan delivery accuracy of VMAT. British Journal of Radiology, 88(1049), 16-24. https://doi.org/10.1259/bjr.20140698.

Pham, A., et al. (2017). Stereotactic Radiosurgery for Multiple Brain Metastases: Two Cases of Preserved Quality of Life. Cureus, 9(12). https://doi.org/10.7759/cureus.1995.

Roper, J. et al. Single-isocenter multiple-target srs: Risk of compromised coverage Int J Radiat Oncol Biol Phys, 93 (2015), pp. 540-546.

Sharpe, M.B. (1995). Extrafocal Radiation: A Unified Approach to the Prediction of Beam Penumbra and Output Factors for Megavoltage X-Ray Beams. Medical Physics, 22(12), 2065-2074. https://doi.org/10.1118/1.597648.

Shiraishi, S., et al. "Knowledge-based prediction of plan quality metrics in intracranial stereotactic radiosurgery." Medical physics 42.2 (2015): 908-917.

Soiza, R. L., et al. "The pale evidence for treatment of iron-deficiency anaemia in older people." (2018): 259-261.

Stanhope, C. et al. "Physics considerations for single-isocenter, volumetric modulated arc radiosurgery for treatment of multiple intracranial targets." Practical radiation oncology 6.3 (2016): 207-213.

Szpala, S., et al. (2014). On using the dosimetric leaf gap to model the rounded leaf ends in VMAT/RapidArc plans. Journal of Applied Clinical Medical Physics, 15(2), 67-84. https://doi.org/10.1120/jacmp.v15i2.4484.

Taillibert, S., et al. (2015). Epidemiology of brain metastases. Cancer/Radiotherapie, 19(1), 3-9. https://doi.org/10.1016/j.canrad.2014.11.001.

Thomas, A., et al. "A comprehensive investigation of the accuracy and reproducibility of a multitarget single isocenter VMAT radiosurgery technique." Medical physics 40.12 (2013): 121725.

Vergalasova, I., et al. (2019). Multi-institutional dosimetric evaluation of modern day stereotactic radiosurgery (SRS) treatment options for multiple brain metastases. Frontiers in Oncology, 9(JUN), 1-12. https://doi.org/10.3389/fonc.2019.00483.

Wu, Q., et al. (2016). Optimization of treatment geometry to reduce normal brain dose in radiosurgery of multiple brain metastases with single-isocenter volumetric modulated Arc therapy. Scientific Reports, 6(June), 1-8. https://doi.org/10.1038/srep34511.

Yao, W., et al. (2015). Determining the optimal dosimetric leaf gap setting for rounded leaf-end multileaf collimator systems by simple test fields. Journal of Applied Clinical Medical Physics, 16(4), 65-77. https://doi.org/10.1120/jacmp.v16i4.5321.

Younge, K. C., et al. "Predicting deliverability of volumetric-modulated arc therapy (VMAT) plans using aperture complexity analysis." Journal of applied clinical medical physics 17.4 (2016): 124-131.

Yuan Y, et al. Evaluation of multiple factors affecting normal brain dose in single-isocenter multiple target radiosurgery. J Radiosurgery SBRT. 2018;5(2):131-144.

Zaila A, et al. Pylinac: A toolkit for performing TG-142 QA related tasks on linear accelerator. Phys Medica. 2016;32:292-293. doi:10.1016/J.EJMP.2016.07.122.

Zhu, T. C., et al. (1995). X-ray source and the output factor. Medical Physics, 22(6), 793-798. https://doi.org/10.1118/1.597588.

\* cited by examiner

SYSTEMS AND METHODS FOR SINGLE ISOCENTER RADIOTHERAPY OF MULTIPLE TARGETS

CROSS-REFERENCE TO RELATED APPLICATIONS

This application claims the benefit of and incorporates herein by reference for all purposes U.S. Provisional Patent Application Ser. No. 62/818,157 filed on Mar. 14, 2019 and entitled "Systems and Methods for Preparing Single Isocenter Multi-Target Treatment Plans."

STATEMENT REGARDING FEDERALLY SPONSORED RESEARCH

N/A

BACKGROUND

Numerous maladies, such as intracranial malignancies, are commonly treated using radiosurgery. For decades, such treatment has been implemented using linear accelerators. Historically, the treatment technique consisted of arcs with conical collimators and more recently has included dynamic conformal arcs (DCA) collimated by High Definition Multi-Leaf Collimators (HDMLC). Multifocal disease has also been treated using a volumetric modulated arc therapy (VMAT) treatment plan.

Brain metastases are the most common neurological complication of primary cancer and are estimated to occur in 9-17% of all cancer patients, with some studies reporting incidence rates as high as 20-40%. Historically, whole-brain radiation therapy (WBRT) has been used to treat metastatic brain lesions but is often associated with degraded neurocognitive functionality. WBRT administered following stereotactic radiosurgery (SRS) may improve local control rates, however, the mean survival time is reduced compared to SRS alone. SRS alone provides superior survival time and cognitive perseveration compared to WBRT and WBRT following SRS. SRS has largely replaced historical methods and has become a standard for treating metastatic brain lesions.

Linear accelerator-based SRS utilizes high precision and steep dose gradients in order to effectively treat the target and spare healthy tissue. Dynamic conformal arcs (DCAs) is a common linear accelerator-based treatment planning technique that has been used to treat brain metastases, for which the multi-leaf collimator (MLC) dynamically conforms to the target throughout gantry rotation. In multi-target treatments, each target is assigned its own isocenter and is treated sequentially, with patient set up and treatment time thus being proportional to the number of isocenters. Treatment time for DCA can be reduced by utilizing a single isocenter dynamic conformal arc (SIDCA) technique. With SIDCA, the MLCs conform to each target (or subgroup of targets per arc); this allows for conformal MLC trajectories which closely conform to targets without creating MLC openings. One challenge for SIDCA is the lack of inverse optimization and thus reduced flexibility to modulate MLCs to accommodate irregularly shaped targets, proximity to critical structures, and the like.

Inverse optimized Volumetric Modulated Arc Therapy (VMAT) has also been applied to multi-target radiosurgery, for which the inverse optimization component provides flexibility to meet unique constraints specific to each plan (such as conforming to irregular shaped targets, minimizing dose to nearby OARs, etc.). Many recent advances have been reported for single isocenter multi-target VMAT radiosurgery, including treatment planning strategies, considerations of physics and quality assurance aspects related to the treatment, and reporting of patient outcomes. One enduring challenge of a single isocenter VMAT technique is the inability of a single leaf pair to collimate multiple targets simultaneously. While strategies have been proposed to minimize aspects of these beam collimation challenges, in many instances targets overlapping with the same leaf pair cannot be eliminated entirely. This becomes increasingly problematic as the number of targets increases. When overlaps do occur, treatment planners must manage the resulting tradeoffs between plan modulation and complexity, target coverage, and dose to normal tissues. Often the resulting inverse optimized VMAT plan will require fast moving and highly modulated MLC trajectories to achieve the desired dose distribution, which has been shown to have a negative effect on dosimetric accuracy.

The success of external beam radiation therapy is reliant on accurate dosimetry and treatment planning system modeling, which may be uniquely challenging when small fields are utilized. The dosimetry and modeling of small radiation fields, which are commonly used in multi-target radiosurgery, is particularly challenging as charged particle equilibrium may fail and targets may be treated off-axis. Disequilibrium paired with steep dose gradients complicates dosimetric measurements and further increases existing uncertainty. For instance, radiosurgery techniques often employ significant collimation, which when paired with a small field, can obscure the primary beam. Substantial blocking of the primary beam may lead to penumbra overlap and a sizable reduction in beam output. Given the dosimetric challenge of small field dosimetry and large treatment doses, it is crucial to evaluate a radiosurgery technique's overall sensitivity and resistance to error.

HD-MLC features rounded leaf pairs to produce relatively constant penumbras at varying field sizes, however, the rounded leaves create a discrepancy in the geometric and dosimetric field widths due to transmission through the rounded edges. The dosimetric leaf gap (DLG) is a parameter that attempts to account for the degree of beam transmission through the rounded leaf edges of the MLC. The configuration of DLG value may introduce uncertainty as a single DLG must be chosen to suit all types of targets, treatment geometries, and MLC systems. The value of the DLG is often optimized such that measured dose distributions for a set of plans match the treatment planning system calculations, making the optimal DLG value dependent on the type of treatment plans and beam model utilized. The plan and model dependency may also be true for multi-target radiosurgery, which is unsurprising given its unique geometry compared to conventional radiation therapy (e.g prostate, breast, head and neck, and the like). Some institutions have even reported difficulty in identifying a single DLG that is representative for all radiosurgery targets, necessitating the need to split targets into multiple isocenter groups, partially negating the time saving benefit of the single isocenter treatment approach.

Proper treatment planning system commissioning may provide for the delivery of accurate and effective treatment plans. Certain aspects of the commissioning process, such as the beam configuration, can impact the quality of clinical performance. The use of small radiation fields, as found in VMAT, may further complicate the commissioning process and the dosimetric accuracy of a treatment. Accurately modeling the dosimetric leaf gap (DLG) poses a challenge as it can drastically affect a treatment plan.

Numerous studies have investigated the commissioning process of determining the DLG value using set field sizes and the sweeping gap technique. In most cases, the DLG value calculated at commissioning does not provide a sufficiently close match between measured and calculated dose, necessitating a further correction of the DLG. In some instances, failing to correct the calculated DLG value may lead to a difference in measured and calculated dose on the order of 5%. While differing DLG values may be required for different types of radiation treatment, some institutional studies have even reported difficulty in determining a single DLG value that is sufficient for all of the institutions' radiosurgery cases. The potential for substantial dose discrepancies and the fact that a single DLG value cannot sufficiently model all treatment plans of a similar type, necessitates a treatment technique that is resistant to DLG variation.

Additional uncertainty may arise from the treatment delivery itself. The physical motion of a given leaf pair may deviate from the ideal MLC motion defined in the treatment planning system and similar deviations in gantry angle also occur during arc delivery. Studies have shown that multi-target radiosurgery techniques are uniquely susceptible to dosimetric effects of these uncertainties, especially when targets are small and/or distant from the isocenter. Furthermore, there are few commercially available QA tools that have sufficient spatial resolution and comprehensive dosimetry to quantify the dosimetric effect of discrepancies that occur at delivery.

Several different treatment techniques have been released in order to attempt to improve the quality of radiosurgery treatment, such as Elements, RapidPlan and HyperArc. Elements (Brainlab, Munich Germany) is an automated software solution for preparing single isocenter dynamic conformal arcs (SIDCA) for multiple brain metastases. RapidPlan (Varian, Palo Alto Calif.) allows for automated creation of VMAT plans. HyperArc (Varian, Palo Alto Calif.) is a VMAT treatment that has been specialized for radiosurgery.

For multifocal disease, multifocal conformal arc techniques can struggle to deliver the desired dose and high conformity for all targets simultaneously. While VMAT is able to achieve better coverage and conformity, it can result in highly modulated, non-intuitive MLC trajectories. The complex MLC trajectories can often struggle with blocking between targets and may leave MLC gaps between targets resulting in increased radiation dose to healthy tissues. Thus there remains a need for a radiotherapy system that provides for the flexibility of VMAT, while also featuring less complex MLC trajectories.

SUMMARY OF THE DISCLOSURE

The present disclosure addresses the aforementioned drawbacks by providing systems and methods for single isocenter radiotherapy of multiple targets. In some configurations, conformal arc information may be used in a Conformal Arc Informed Volumetric Modulated Arc Therapy (CAVMAT) method that includes single isocenter radiotherapy of multiple targets where conformal multi-leaf collimator (MLC) trajectories may be used as the starting point of limited inverse optimization. Single isocenter radiotherapy of multiple targets may retain the flexibility of VMAT, while maintaining less complex MLC trajectories, and fully block between targets with the MLC.

In one configuration, a method is provided for controlling a radiation therapy system. The method includes assigning radiotherapy targets into a target subgroup for an arc geometry and generating a conformal arc based on the arc geometry to maximize blocking between the radiotherapy targets of the target subgroup for radiotherapy. The method also includes determining an initial radiotherapy dose based upon the conformal arc and generating weighted conformal arcs by determining field weights to deliver a radiotherapy dose with a conformity to the radiotherapy targets. The method also includes performing an inverse optimization process on the weighted conformal arcs to adjust the radiotherapy dose and the conformity of the target subgroup, and determining a final dose for the radiotherapy targets.

In one configuration, a system is provided for controlling a radiation therapy system. The system includes a computer system configured to: a) assign radiotherapy targets into a target subgroup for an arc geometry; b) generate a conformal arc based on the arc geometry to maximize blocking between the radiotherapy targets of the target subgroup for radiotherapy; c) determine an initial radiotherapy dose based upon the conformal arc; d) generate weighted conformal arcs by determining field weights to deliver a radiotherapy dose with a conformity to the radiotherapy targets; e) perform an inverse optimization process on the weighted conformal arcs to adjust the radiotherapy dose and the conformity of the target subgroup; and f) determine a final dose for the radiotherapy targets.

In one configuration, a computer readable medium is provided. The computer readable medium including instructions stored on the computer readable medium for assigning a plurality of radiotherapy targets into a plurality of target subgroups for a plurality of arc geometries. The instructions also include generating conformal arcs based on the arc geometries to maximize blocking between the plurality of radiotherapy targets of the plurality of target subgroups for radiotherapy. The instructions also include determining initial radiotherapy doses based upon the conformal arcs and generating weighted conformal arcs by determining field weights to deliver a radiotherapy dose with a conformity to the plurality of radiotherapy targets. The instructions also include performing an inverse optimization process on the weighted conformal arcs to adjust the radiotherapy dose and the conformity of the plurality of target subgroups; and determining a final dose for the plurality of radiotherapy targets.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
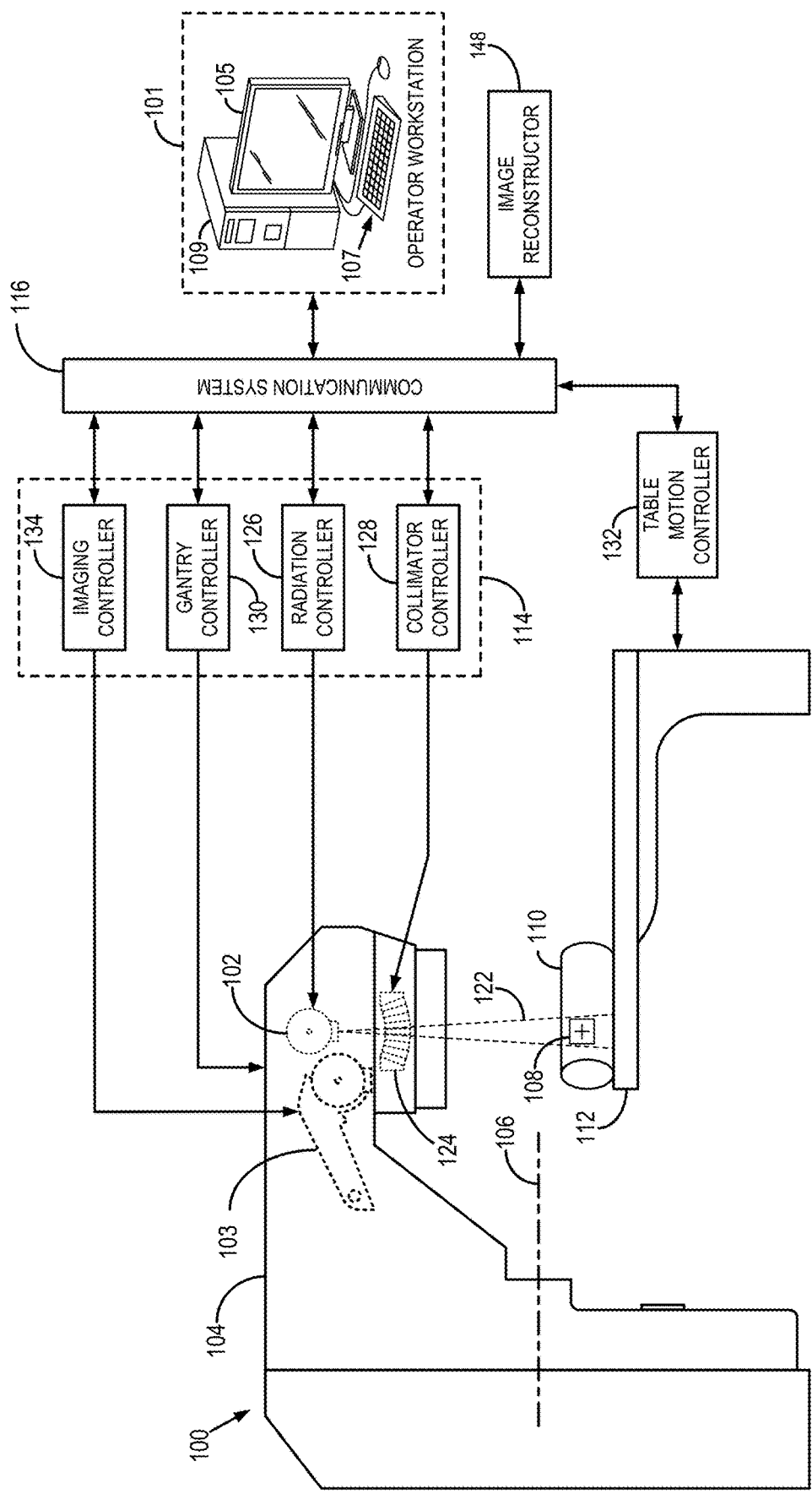
FIG. 1 is a block diagram of a radiation therapy system that may be used in accordance with the present disclosure.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to radiotherapy are disclosed. It should be apparent to those skilled in the art that many additional modifications besides those already described are possible without departing from the inventive concepts. In interpreting this disclosure, all terms should be interpreted in the broadest possible manner consistent with the context Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10. "About" is used to provide flexibility to a numerical range endpoint by providing that a given value may be "slightly above" or "slightly below" the endpoint without affecting the desired result. The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

Systems and methods for single isocenter radiotherapy of multiple targets are provided. In some configurations, conformal arc information may be used in a Conformal Arc Informed Volumetric Modulated Arc Therapy (CAVMAT) method. CAVMAT may include conformal multi-leaf collimator (MLC) trajectories, which may be used as the starting point for a limited inverse optimization and a resulting final dose calculation. Single isocenter radiotherapy of multiple targets may provide flexibility with less complex MLC trajectories, and fully block between targets with the MLC. By providing for both the advantages of conformal MLC motions of DCA plans with flexible MLC modulation of limited inverse optimization, the systems and methods can produce clinically viable plans of high quality (low dose sparing & conformity) and with decreased plan complexity.

SRS has been shown to increase the risk of neurological complications when treating brain metastases. Radionecrosis may occur in a substantial percentage of SRS patients and may be associated with neurological complications such as speech or motor deficits. Single isocenter radiotherapy of multiple targets, such as the CAVMAT treatment planning technique, reduces the risk of radionecrosis and neurological complications. In some configurations, single isocenter radiotherapy of multiple targets overcomes the challenge of blocking healthy tissue between targets by utilizing sub-grouping and effective field weighting, to create an intuitive starting point for inverse optimization. The limited inverse optimization adds a level of flexibility in MLC modulation to adjust to complex geometries and further improve upon dose conformity.

Referring to FIG. 1, a non-limiting example radiation therapy system 100 is shown that includes a therapeutic radiation source 102 and an on-board imaging source 103. The radiation source 102 and the on-board imaging source 103 may be housed in the same gantry system 104 or may be mounted orthogonally to the radiation source 102. The radiation therapy system 100 may include any suitable radiation treatment system, including image-guided radiation therapy ("IGRT") systems, intensity-modulated radiation therapy ("IMRT") systems such as intensity-modulated arc therapy ("IMAT") and volumetric modulated arc therapy ("VMAT") systems, an external beam radiotherapy delivery system, such as a linear accelerator (LINAC), proton radiotherapy systems, slice by slice photon radiotherapy systems (Tomotherapy), non-isocentric photon radiotherapy systems (Cyberknife), and isotope based radiotherapy systems (ViewRay and GammaKnife), and the like. In a non-limiting example, the radiation therapy system is a Truebeam STX linear accelerator with MV photons and HD-Multileaf Collimators (MLC). The treatment beam for the radiation therapy system can be composed of photons, neutrons, electrons, protons, heavy charged particles, or the like. Specific treatment plans can also be designed and delivered in order to evaluate key parameters of each radiotherapy system. Clinically relevant treatment plans can be prepared and utilized for end-to-end testing.

The on-board imaging source 103 may include an x-ray source, a Cone-Beam Computed Tomography (CBCT) system, a Computed Tomography (CT) system, a 4DCT system, a magnetic resonance imaging (MRI) system, and the like. Alternatively, the imaging may be performed by a separate diagnostic imaging system. Both the therapeutic radiation source 102 and imaging source 103 are attached adjacent each other and housed at the same end of a rotatable gantry 104, which rotates about a pivot axis 106. The rotatable gantry 104 allows either of the sources, 102 and 103, to be aligned in a desired manner with respect to a target volume 108 in a subject 110 positioned on a table 112.

The rotation of the rotatable gantry 104, the position of table 112, and the operation of the sources, 102 and 103, are governed by a control mechanism 114 of the radiation therapy system 100. The control mechanism 114 includes a radiation controller 126 that provides power and timing signals to the radiation source 102, an imaging controller 134 that provides image acquisition instructions to imaging source 103, and receives image data therefrom, and a gantry motor controller 130 that controls the rotational speed and position of the gantry 104. The control mechanism 114 communicates with an operator workstation 101 and other parts of a network through communication system 116. An image reconstructor 148, receives sampled and digitized image data from the communication system 116 and performs high speed image reconstruction. The reconstructed image is applied as an input to a computer 109.

The computer 109 also receives commands and scanning parameters from an operator via a console that has a keyboard 107. An associated display 105 allows the operator to observe the reconstructed image and other data from the computer 109. The operator supplied commands and parameters are used by the computer 109 to provide control signals and information to the imaging controller 134, the radiation controller 126 and the gantry motor controller 130. In addition, the computer 109 operates a table motor controller 132 which controls the motorized table 112 to position the subject 110 within the gantry 104.

Still referring now to FIG. 1, radiation source 102 produces a radiation beam, or "field," 122, which in some forms may be conical or any other shape, emanating from a focal spot and directed toward a subject 110. The radiation beam 122 may be initially conical and is collimated by a collimator 124 constructed of a set of rectangular shutter system blades to form a generally planar "fan" radiation beam 122 centered about a radiation fan beam plane. Each leaf of the collimator is constructed of a dense radio-opaque material such as lead, tungsten, cerium, tantalum, or related alloy.

A collimator control system 128 directed by a timer generating desired position signals provides electrical excitation to each electromagnet to control, separately, actuators to move each of the leaves in and out of its corresponding sleeve and ray. The collimator control system 128 moves the leaves of the collimator 124 rapidly between their open and closed states to either fully attenuate or provide no attenuation to each ray. Gradations in the fluence of each ray, as needed for the fluence profile, are obtained by adjusting the relative duration during which each leaf is in the closed position compared to the relative duration during which each leaf is in the open position for each gantry angle. Alternatively, a physical cone or other structure may be used in place of the multi-leaf collimator.

The ratio between the closed and open states or the "duty cycle" for each leaf affects the total radiation fluence passed by a given leaf at each gantry angle, θ, and thus controls the average fluence of each ray. The ability to control the average fluence at each gantry angle, θ, permits accurate control of the dose provided by the radiation beam 122 through the irradiated volume of the subject 110 by therapy planning methods to be described below. The collimator control system 128 also connects with a computer to allow program control of the collimator 124 to be described.

An image reconstructor 148, typically including a high speed array processor or the like, receives the data from the imaging controller 134 in order to assist in "reconstructing" an image from such acquired image data according to methods well known in the art. The image reconstructor 148 may also use post-radiation detector signals from a radiation detector to produce a tomographic absorption image to be used for verification and future therapy planning purposes.

In some configurations, a method of performing single isocenter radiotherapy of multiple targets, such as the CAVMAT method, may include target subgrouping, field weight optimization, and limited inverse optimization. Sets of conformal arcs may be created that sufficiently collimate between targets and avoid dose bridging. Optimal weighting may be assigned to the conformal arcs, and a limited inverse optimization may be performed to increase dose conformity around the targets and meet any dosimetric constraints that are unique to the treatment plan.

Figure 2:
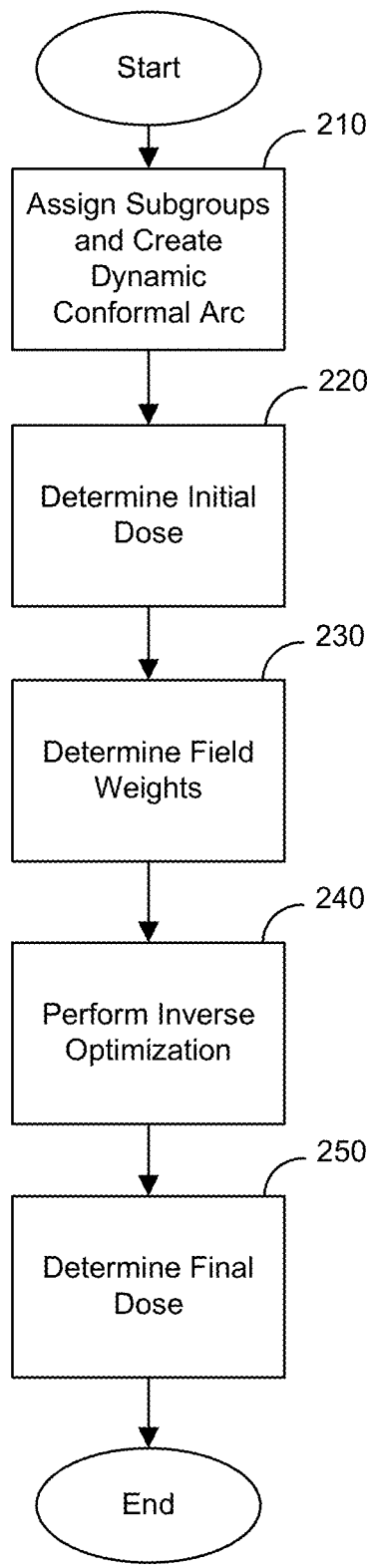
FIG. 2 is a flowchart of non-limiting example steps for a method of performing single isocenter radiotherapy of multiple targets in accordance with the present disclosure.

Referring to FIG. 2, a flowchart of non-limiting example steps for a method of performing single isocenter radiotherapy of multiple targets is provided. Conformal arcs may be assigned to subgroups of targets to maximize blocking between targets at step 210. The initial dose may be determined or calculated at step 220. The arc or field weights to achieve a desired dose per target while minimizing the variation in MU per arc may be determined or optimized at step 230. An inverse optimization process, such as a VMAT optimization process, may be performed to fine tune the dose to each target and optimize conformity at step 240. The final dose may be determined or calculated at step 250 after the inverse optimization at step 240.

Figure 4B:
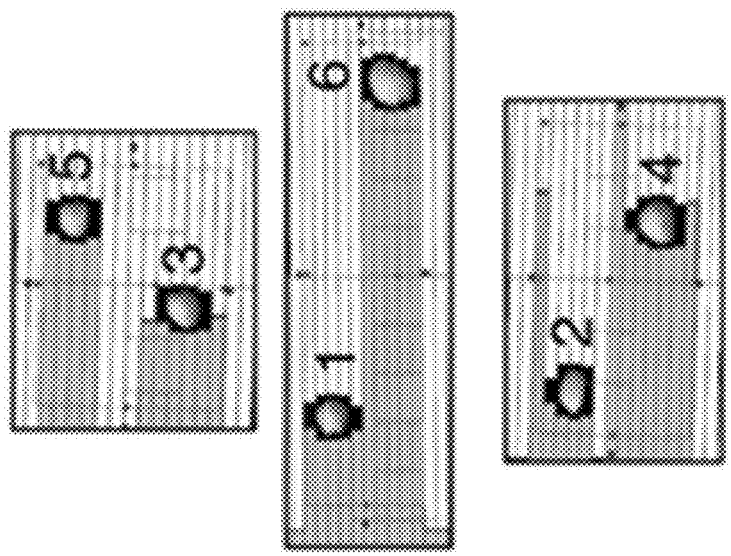
FIG. 4B is a non-limiting example of a beam's eye view and MLC shape of a plan in accordance with one aspect of the present disclosure.
Figure 4A:
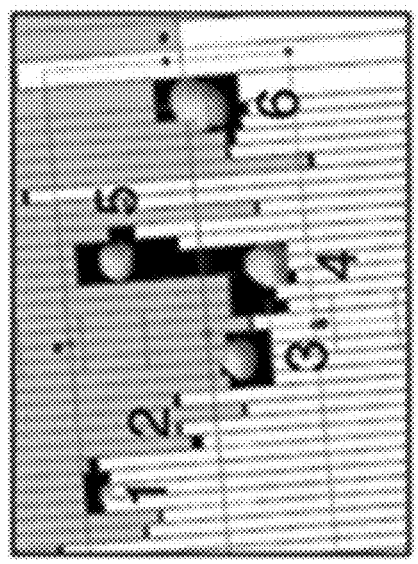
FIG. 4A is a non-limiting example of a beam's eye view and MLC shape of a VMAT plan.

At step 210, conformal arcs may be assigned subgroups of targets to maximize blocking between targets. As described below, blocking of targets is depicted in FIGS. 4A and 4B. Each arc may be planned to treat subgroups of targets, keeping the clinical plan gantry geometries and changing collimator angles for optimal MLC conformality to the targets considered for the subgroup. In some embodiments, subgroups of targets may be selected prioritizing variability of target combinations per subgroup and island blocking.

Figure 3:
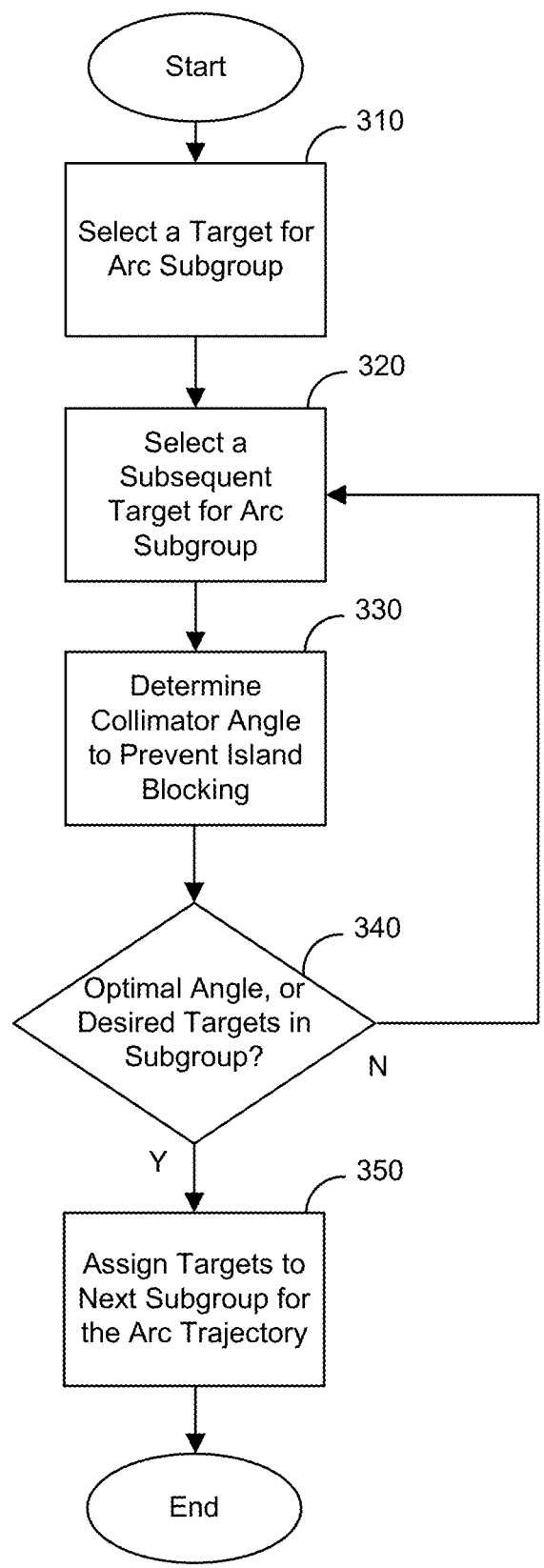
FIG. 3 is a flowchart of non-limiting example steps for a method of selecting a subgroup of targets in accordance with the present disclosure.

Referring to FIG. 3, a flowchart of non-limiting example steps for a method of selecting a subgroup of targets is shown. A target may be selected for an arc subgroup at step 310. Target subgroups are selected such that a collimator angle can be found to appropriately block between multiple targets. Target superposition is also considered and avoided in the subgrouping process as it may lead to dose bridging between targets. Targets may be selected manually or in an automated fashion. In some configurations, the first target may be selected randomly. A second or subsequent target may be selected at step 320. Selection of a second or subsequent target may be performed randomly, or may follow a priority list as described below. An optimal collimator angle to prevent island blocking may be determined at step 330. If an optimal collimator angle does not exist, steps 320 and 330 may be repeated according to step 340. In a non-limiting example, steps 320 and 330 may be repeated until about half the targets are in the subgroup. If an optimal angle or the desired number of targets are in the subgroup according to step 340, the remaining targets may be assigned into a second or subsequent subgroup for the same arc trajectory, or for a new arc trajectory at step 350. In certain embodiments, variability is created in the subgroup so no two subgroups have the same combination of targets. Any number of target subgroups or arcs may be used.

Any arrangement of arcs may be used that are suitable for radiosurgery. For each gantry and couch angle, targets may be treated by dividing them into subgroups containing as many targets as possible while still fulfilling all criteria. Each subgroup may be assigned a copy of the arc, to be treated separately.

In some configurations, targets may be selected manually, or automatically. For the first subgroup of an arc, the first target may be selected at random. Subsequent targets may be added to the subgroup according to a priority list. In non-limiting examples, the priorities may include the criteria of: a collimator angle can be found to completely collimate between targets; target superposition (i.e. when one target appears to move directly in front or behind another target in the beam's eye view) is not present; average effective depth of the targets in the subgroup are not largely different (in a non-limiting example, less than 5 cm); when all previous criteria can be met, unique subgroups—or unique subsets of targets—across all arcs in the plan may be created. When none of these criteria can be met, a new subgroup may be created. Of these criteria, complete collimation and target superposition may work together to prevent dose bridging between targets. Average effective depth may avoid dose disparities between targets that can be difficult to counteract during the field weight optimization—prior to inverse optimization each arc may have constant MU per control point Meeting all of the criteria may be prioritized to increase the effectiveness of the field weight optimization which seeks to apply a uniform MU to each arc to achieve the desired target dose prior to a conventional inverse optimization standard to VMAT.

The method of target selection may be repeated for each arc in the treatment plan such that each arc may have a unique set of subgroups. The number of subgroups per arc may be dependent on the geometry of the targets and the arc itself. As stated above, any number of subgroups may be used. In a non-limiting example, the number of subgroups for a case may be from 1 to 3. Once the subgroups for each arc are created, each subgroup may be given a copy of the arc.

In a non-limiting example, if a plan with 4 couch angles (with 1 arc each) is assigned 2 subgroups per arc, the resultant plan would still have 4 couch angles, but now with 2 arcs at each couch angle. Each of those 2 arcs per couch angle may be treating a single subgroup of targets. For efficiency of delivery, the direction of these arcs can then be optimized to move in opposite directions (i.e. starting with clockwise rotation for the first sub-arc, followed by counter-clockwise for the subsequent, and the like).

Following subgroup assignment, the MLCs for each arc may be fit to collimate around each target. In a non-limiting example, the MLCs may be fit to a 1 mm margin and the jaws to a 3 mm margin around the maximum target distance in each axis projected in the beam's eye view for the subgroup of targets assigned to that arc. Margins may be chosen based upon whether the inverse optimization prevents the MLC leaf pairs from fully opening to the field size set by the jaws or not. Preventing the MLC from fulling opening may be particularly apparent in cases involving small targets and small field sizes, often resulting in under coverage. The use of jaw tracking may be used, or fixed jaw settings may be used.

Referring again to FIG. 2 and step 230, after subgroup creation and arc assignment, weighting of each subgroup arc may be optimized to achieve desired dose per target while minimizing the variation in monitor units (MU) per arc. Weighting may be provided by any appropriate means or algorithm. Non-limiting examples include stochastic minimization routines, nonlinear minimization routines, a Nelder-Mead multidimensional nonlinear minimizer and the like.

The MU for each subgroup of conformal arcs may be fixed for each field, and each field's dose contribution to a point in every target may be measured. A fixed MU for each field may be used as a starting point for later modifications in a treatment planning system. In some embodiments, field weight optimization may be directly integrated into the treatment planning system, or it may be performed using a separate software tool. In some embodiments, point dose is calculated at the center of each target to determine $d_{tf}$, the dose contribution to a target t from a field f. The dose difference to be minimized can be represented by:

$$\Delta D = |D_{Rx} - \Sigma_f (d_{tf} \times W_f)| \quad (1)$$

Where D is the dose to target t and $d_{tf}$ is the dose contribution to target t by field f, and $W_f$ is the weighting of field f. A field weight optimization algorithm may be used to iteratively adjust field weights $W_f$ to match the prescription dose of $D_{Rx}$ and improve uniformity of field weights across all arcs. In some embodiments, dose to the entire target may be calculated and the field weight optimization may be performed so as to achieve a desired dose volume constraint for each target, such as the minimum dose delivered to 95% of the target volume.

In some configurations, the field weights may be adjusted using a Nelder-Mead multidimensional nonlinear minimizer and the dose contribution from each arc to each target. The Nelder-Mead algorithm generates a simplex and uses its vertices to minimize multidimensional functions to find a local minimum. The simplex may be first reflected, and the reflected point is then compared to the current best minimum. The vertex with the largest value may be replaced by a new, smaller vertex. This reduction process may continue until the coordinates of the local minimum are determined. In a non-limiting example, a contraction coefficient of 0.5 may be used in order to determine the strength and rate that the simplex converges to a minimum. For each iteration, a single initial field weight may be reduced by 50%, creating multiple sets of final field weight solutions.

In a non-limiting example, when considering N number of fields, or arcs in the treatment plan, the method repeats the optimization N times, with one field weight decreased by 50%, resulting in N+1 field sets, which weights the difference between prescribed dose and calculated dose per target. An optimized conformal arc plan may then serve as the starting point in an inverse optimization, such as VMAT inverse optimization, to fine tune the dose to each target and optimize conformity. In some configurations, the field weight optimized plan is put through an inverse optimization algorithm (in a non-limiting example). The final dose may be recalculated after the inverse optimization.

The field weight sets may be used to find the new MU for each arc, and may be ranked based on absolute difference in prescription and delivered target dose; standard deviation of the difference in prescription and delivered target dose; the number of fields that have <10% of the median MU; the standard deviation of the MU per arc, and the like. These ranking criteria may each be given equal weighting and the field weight set with the highest average ranking in all four categories was used to determine the new MU for the treatment plan Referring again to FIG. 2 and step 240, after MU per subarc is determined through the field weight optimization, the result may be a multiple target single isocenter dynamic conformal arc plan, which can then be used as the starting point for a limited inverse optimization, such as a VMAT inverse optimization. The most optimal field weights may be provided to a treatment planning system configured to implement a limited inverse optimization. In a non-limiting example, the inverse optimization may be performed in a system such as an Eclipse version 15.6 (Varian Medical Systems, Palo Alto, Calif.) using the Progressive Optimization (PO) algorithm 15603, which may be limited to multi-resolution (MR) level 4. Limiting the optimization resolution to MR4 may allow methods in accordance with the present disclosure to conform to targets while still maintaining relatively similar MLC trajectories to conformal arcs, but may also allow the optimizer to make small, fine-tuned MLC adjustments. Following inverse optimization, the plans may be re-normalized such that 100% of the prescription dose may be applied to 99.5% of the total PTV volume. In another non-limiting example, the inverse optimization may be performed on a stand-alone system. One skilled in the art will appreciate that other dose applications to other volumes may be provided.

With the final dose determined in step 250 of FIG. 2, the methods and systems may provide for a planning technique that allows for smaller low dose spill to normal brain tissue compared to VMAT, with comparable conformity, monitor units, and treatment times.

Non-Limiting Example VMAT Comparison

Referring to FIGS. 4A and 4B, a non-limiting example of a beam's eye view and MLC shape of VMAT (FIG. 4A) and a CAVMAT method in accordance with the present disclosure (FIG. 4B) are shown for one field of one case. FIG. 4A illustrates the inherent inability of a single leaf pair to collimate multiple targets simultaneously, while FIG. 4B illustrates the CAVMAT strategy to mitigate this challenge. The target subgroups in FIG. 4B allow the MLCs to conform closely to the targets of an arc, without pushing the inverse optimization to over-modulation. The CAVMAT technique separates the six targets into three subgroups with two targets each, and configures the MLCs such that all six targets may be treated without the need to utilize a single leaf pair to collimate multiple targets simultaneously. Targets 3 and 5 are placed in a first subgroup, targets 1 and 6 are placed in a second subgroup, and targets 2 and 4 are placed in a third subgroup.

Figure 5:
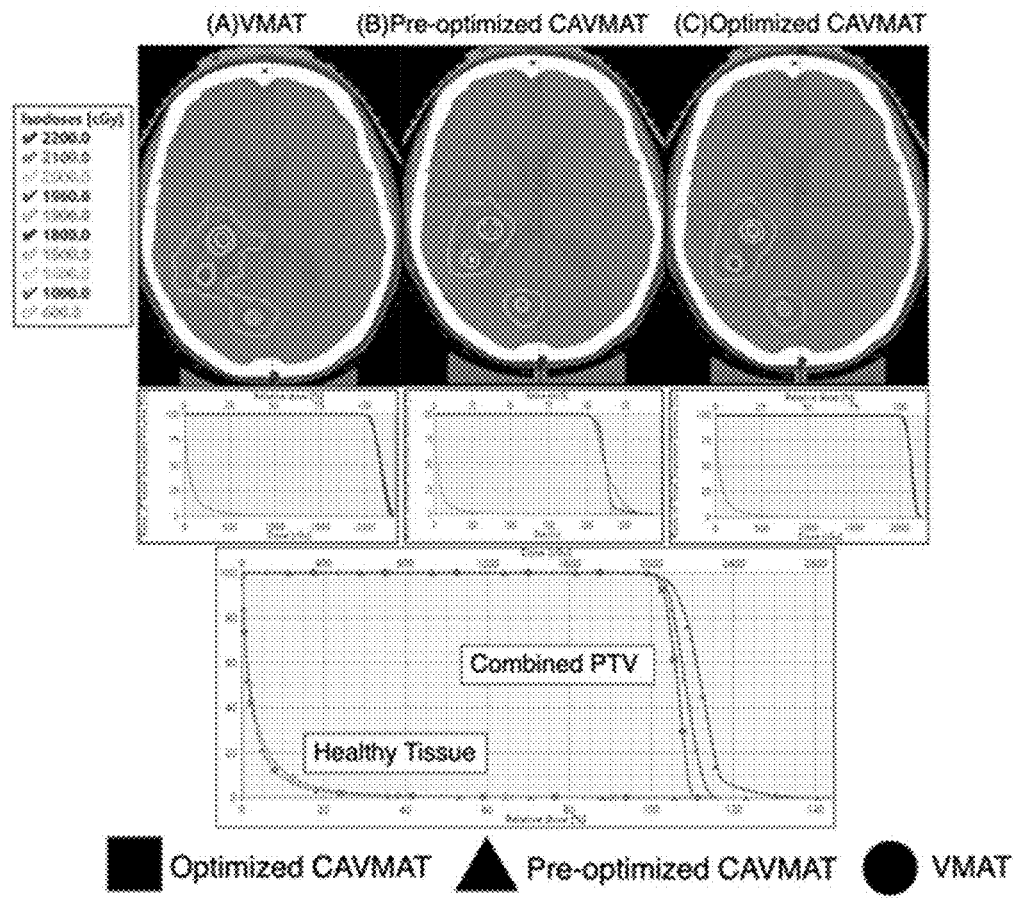
FIG. 5 is a graph of non-limiting example data comparing VMAT to a plan in accordance with one aspect of the present disclosure.

As indicated in FIG. 5, the pre-optimized CAVMAT plan produced a smooth isodose distribution. For this non-limiting example, the pre-optimized CAVMAT plan reduced the $V_{2.5Gy\;[cc]}$ of heathy tissue by 26.08% (82.18 cc), $V_{6Gy\;[cc]}$ by 27.71% (17.49 cc), $V_{12Gy\;[cc]}$ by 28.21% (3.77 cc), and $V_{16Gy\;[cc]}$ by 11.33% (0.69 cc). Following limited inverse optimization, the resulting CAVMAT plan had a more concentric, smooth, and less heterogeneous isodose distribution than both the pre-optimized CAVMAT and VMAT. The optimized CAVMAT plan reduced the $V_{2.5Gy}$ of total tissue by 25.60% (82.18 cc), $V_{6Gy\;[cc]}$ by 24.68% (15.59 cc), $V_{12Gy\;[cc]}$ by 25.18% (3.37 cc), and $V_{16Gy\;[cc]}$ by 14.14% (0.86 cc). In some configurations, the limited inverse optimization may reduce the tissue sparing marginally for a large gain in conformity.

Non-limiting Intracranial Cases Example

In a non-limiting example, twenty intracranial radiosurgery cases, previously treated using Volumetric Modulated Arc Therapy (VMAT), were selected and reviewed. Each selected case contained between three and seven metastases. Only cases that were treated in a single fraction were included which limited target size to a diameter ≤2 cm. The 20 cases and corresponding targets are summarized below in Table 1.

TABLE 1

| | |
|---|---|
| Total Number of Targets | 77 |
| Mean Targets per Plan | 3.85 ± 1.18 |

TABLE 1-continued

| | |
|---|---|
| Total Target Volume | 46.29 cc |
| Mean Target Volume per Plan | 2.31 ± 1.79 cc |
| Maximum Target Volume | 6.02 cc |
| Minimum Target Volume | 0.22 cc |

While CAVMAT may be applied to any combination of prescription doses, in this non-limiting example all cases were prescribed 20 Gy to each target in order to simplify dose-volume statistics. Treatment planning for the original VMAT plans was performed in External Beam Planning (Varian Medical Systems) using the Anisotropic Analytical Algorithm (AAA) for dose calculation with a 1 mm dose voxel size. In each case the treatment plan was prepared by an ABR certified physicist with experience in clinical VMAT SRS planning, after which it was reviewed and approved by the attending physician. Of the 20 total cases selected, 11 plans featured prescription doses less than 20 Gy or utilized multiple fractions and were re-planned with 20 Gy applied to each target to simplify the reported statistics. Re-planning was also performed by an ABR certified physicist with experience in clinical VMAT SRS planning.

All cases were re-planned with the CAVMAT technique. To minimize the number of variables in the comparison, CAVMAT plans were limited to the same geometry as the clinically delivered VMAT plans and arc geometry: gantry stop and start angles, and couch angles were not adjusted. The collimator angle of the CAVMAT plans was adjusted in the subgrouping process. Thus, the CAVMAT plans had the same plan geometry as VMAT, but with the number of arcs at each couch angle being equal to the number of CAVMAT subgroups. All plans were normalized such that 100% of the prescription dose was delivered to 99.5% of the combined PTV volume.

The cumulative DVHs of the clinical VMAT and CAVMAT plans were analyzed and compared. For each VMAT plan, the total volume receiving 2.5 Gy ($V_{2.5Gy\;[cc]}$), $V_{6Gy\;[cc]}$, $V_{12Gy\;[cc]}$, $V_{16Gy\;[cc]}$, maximum dose ($D_{max}$), and total MU was measured and compared to its CAVMAT counterpart. The percent change of $V_{2.5Gy\;[cc]}$, $V_{6Gy\;[cc]}$, $V_{12Gy\;[cc]}$, $V_{16Gy\;[cc]}$, and total MU between the VMAT and CAVMAT plans was calculated. The limiting target coverage (coverage of the target with the lowest percentage of volume receiving the prescription dose) of both VMAT and CAVMAT was measured and compared. Conformity index (CI) was measured and was defined as the volume enclosed by the prescription isodose surface ($V_I$) divided by the total target volume ($V_t$)

$$CI = \frac{V_I}{V_t} \qquad (2)$$

Total treatment time for each plan was estimated using the control points, dose rate, and gantry speed of each arc. Each control point was evaluated and treatment time was calculated as the summation of the time necessary to move from one control point to the next.

$$\sum_{i=0}^{n}\left(\frac{MU_i}{MaxDoseRate} \text{ or } \frac{Angle_i}{MasGantrySpeed}\right) \qquad (3)$$

The treatment time between two individual control points was determined based on whether dose rate or gantry speed was the limiting factor, as both may not be maximized simultaneously. While MLC velocity was theoretically a limiting factor in treatment delivery time, both the VMAT and CAVMAT plans were never found to be limited by MLC velocity. The summation was calculated for whichever factor impeded the total treatment time most substantially. A Wilcoxon signed rank test was used to evaluate and compare the maximum dose, conformity index, dose-volume statistics, and limiting target coverage VMAT and CAVMAT plans. The Wilcoxon test is a non-parametric test and was used to compare matched samples. p values <0.05 were considered to be statistically significant.

Considering all twenty plans, CAVMAT reduced the average $V_{2.5Gy\ [cc]}$ of total tissue by 25.25±19.23% (66.35±58.93 cc) (p=8.85×10$^{-5}$), $V_{6Gy\ [cc]}$ by 13.68±18.97% (6.33±5.07 cc) (p=0.027), $V_{12Gy\ [cc]}$ by 11.40±19.44% (1.32±1.12 cc) (p=0.048), and $V_{16Gy\ [cc]}$ by 6.38±19.11% (0.63±0.38 cc) (p=0.247). CAVMAT accomplished this tissue sparing while still maintaining an average maximum target dose of 21.99 Gy, compared to 22.78 Gy for VMAT. A Wilcoxon signed rank test between the VMAT and CAVMAT maximum dose values yielded a significant p value of 8.84×10$^{-5}$.

Across the twenty cases, the average conformity index (CI) for VMAT was 1.40±0.19. For pre-optimized CAVMAT the CI increased to 1.63±0.32 (increase of 16.4±17.27% from VMAT). In contrast, for the post-optimization CAVMAT plans the CI was 1.34±0.15 (decrease of 3.81%±7.57% from VMAT) (p=0.026). CAVMAT maintained the high limiting target coverage of VMAT, with no significant observed difference in coverage (p=0.49).

The total MU of the pre-optimized CAVMAT plans increased by 29.40±26.40% (compared to VMAT), with the inverse optimized CAVMAT plans utilizing roughly 5% less MU than the pre-optimized DCA plans. Compared to VMAT, the average total MU of the inverse optimized CAVMAT plans increased by 24.35±24.66% (1507.70±1182.23). This indicated that dividing the targets of an arc into subgroups required more MU to adequately treat all targets The increased MU and use of subgroups lead CAVMAT to slightly increased treatment delivery time. The CAVMAT plans have an average of 7.55±1.85 arcs per plan compared to 3.75±0.64 arcs for VMAT, which accounted for the time differences. While the CAVMAT plans had roughly twice the arcs of the VMAT plans, the treatment time was not doubled, but rather the average estimated treatment time increased slightly. This was partially due to the fact that the CAVMAT plan had the same treatment geometry as the VMAT plan (couch angles and gantry rotation); the additional arcs were duplicate arcs of the base VMAT plan, where the CAVMAT plan rotated the gantry clockwise and then counter-clockwise at each couch angle to deliver the subgroup arcs. The VMAT plan delivery was almost always limited by dose rate.

In the non-limiting example, all targets were assigned a prescription dose of 20 Gy in order to facilitate the reporting of dose statistics. One skilled in the art would appreciate that the targets for other treatment scenarios may be assigned different doses if they are close to a critical organ or have been treated previously. The methods in accordance with the present disclosure do not require adaptation to treat targets at different doses; the subgrouping method may remain unchanged. In some configurations for targets with different doses, the field weight optimization may be adjusted where the desired target dose can be set, and the inverse optimization constraints may be adjusted.

Non-Limiting Example DLG and Mechanical Treatment Errors

In the non-limiting example, ten previously treated single isocenter VMAT cases were selected and re-planned with a CAVMAT method, in accordance with the present disclosure. Each non-limiting example case included 3 to 7 brain metastases. Only cases that were prescribed a single fraction of 20 Gy were utilized, restricting target size to ≤2 cm in equivalent sphere diameter. In total, 46 targets were included and analyzed. Varian Eclipse 15.6 (Varian Medical Systems) was used for the treatment planning of the original VMAT plans, and the CAVMAT plans. The plans were calculated using Anisotropic Algorithm (AAA) with a 1 mm dose voxel size. Each case was prepared by an ABR certified physicist with experience in clinical VMAT SRS treatment planning and was reviewed and approved by the attending physician. Of the 10 VMAT cases included, 3 were re-planned to ensure that all targets received the prescription dose of 20 Gy. All targets were prescribed 20 Gy in order to simplify the reported statistics and to make the results more uniform and significant.

The 10 VMAT and CAVMAT cases were both calculated at varying DLG values of 0.4 mm, 0.8 mm, and 1.2 mm, creating sixty different plans. All cases were first calculated with a 0.4 mm DLG, establishing a baseline for subsequent comparison. The same MU per arc was used when calculating all DLG plans and normalization was not utilized.

The volume of healthy tissue receiving 6 Gy ($V_{6Gy\ [cc]}$), $V_{12Gy\ [cc]}$, $V_{16Gy\ [cc]}$ of the VMAT and CAVMAT plans were collected and compared. The minimum, mean, and maximum dose to all 46 targets was also collected. The percent change in dose statistics and conformity index was used to quantitatively compare plans of differing DLG, using the 0.4 mm DLG as a baseline. Target volume, equivalent sphere radius, and distance from radiation isocenter were also measured and recorded. The limiting coverage ($D_{99\%[\%]}$) for each target was evaluated at all 3 DLG values.

A modulation complexity score (MCS) script for the 10 VMAT and CAVMAT plans was used to determine the overall complexity and equivalent field sizes of the CAVMAT and VMAT plans, with a constant DLG setting of 0.4 mm. The MCS implementation evaluates the leaf sequence variability (LSV) and aperture area variability (AAV) in order to assess variation in MLC position, field shape irregularity, and field area. MCS values range from 0 to 1.0, with an open, non-modulated field receiving a score of 1.0 and a highly modulated plan receiving scores approaching 0.

The 10 VMAT and CAVMAT plans, featuring 46 targets in total, were prepared for delivery and were uploaded. The 10 plans were delivered using a radiotherapy system. In order to minimize variability, all plans were delivered using the same linear accelerator that was used for the delivery of the clinical VMAT plans. Following treatment delivery, the delivered (actual) MLC positions of both the VMAT and CAVMAT plans were automatically stored as trajectory log files in the system. A script was used to scan the trajectory log files and to extract the delivered MLC and gantry positions for each arc control point. Then, a copy of the original plan was created where the original MLC and gantry positions were overwritten with the positions recorded in the log files. The updated plans were re-imported into the treatment planning system to construct an accurate representation of the plan that the linear accelerator delivered. The delivered plans were calculated with the same total MU, AAA algorithm, and dose grid size as the original treatment plans.

The planned VMAT and CAVMAT plans were analyzed and compared to the delivered plans to assess the dosimetric change in the plans and general sensitivity to treatment delivery. The volume of healthy tissue receiving 6Gy ($V_{6Gy\ [cc]}$), $V_{12Gy\ [cc]}$, and $V_{16Gy\ [cc]}$ was measured directly from the plan DVH. The minimum, mean, and maximum dose to all 46 targets was collected. The total plan conformity index (CI) for the planned and delivered treatment plans was measured and evaluated. The coverage of each target was measured for all planned and delivered VMAT and CAVMAT plans.

The trajectory log files were used to determine the MLC leaf position at each control point of the VMAT and CAVMAT arcs. The relative MLC position error at each control point was quantified as the absolute difference between planned and delivered MLC position.

Following treatment delivery, a phantom was used to conduct gamma analysis on the VMAT and CAVMAT delivered plans. Several different passing criteria, with increasingly strict margins, were used to assess plan robustness. The absolute difference between planned and delivered dose and the distance to agreement (DTA) was evaluated at 3%, 2%, and 1% margins. Gamma analysis was performed using 3%/1 mm, 2%/1 mm, and 1%/1 mm passing criteria for both the VMAT and CAVMAT plans.

16 of the 46 total targets, with at least 1 target from each plan, were selected to be delivered to a QA phantom. For each target, a QA verification plan was created with a constant DLG values of 0.4 mm. The QA plans were delivered using the same linear accelerator that was used for the previous plans. The 16 VMAT and CAVMAT QA verification plans were then recalculated at DLG values of 0.8 mm and 1.2 mm. The delivered 0.4 mm DLG dose distributions were used as a baseline and were compared against the calculated 0.8 mm and 1.2 mm plans to determine dose difference. The dose difference for all VMAT and CAVMAT plans, at all three DLG values, was collected at a threshold of 50% to quantify dose difference sensitivity to DLG variation.

Figure 6:
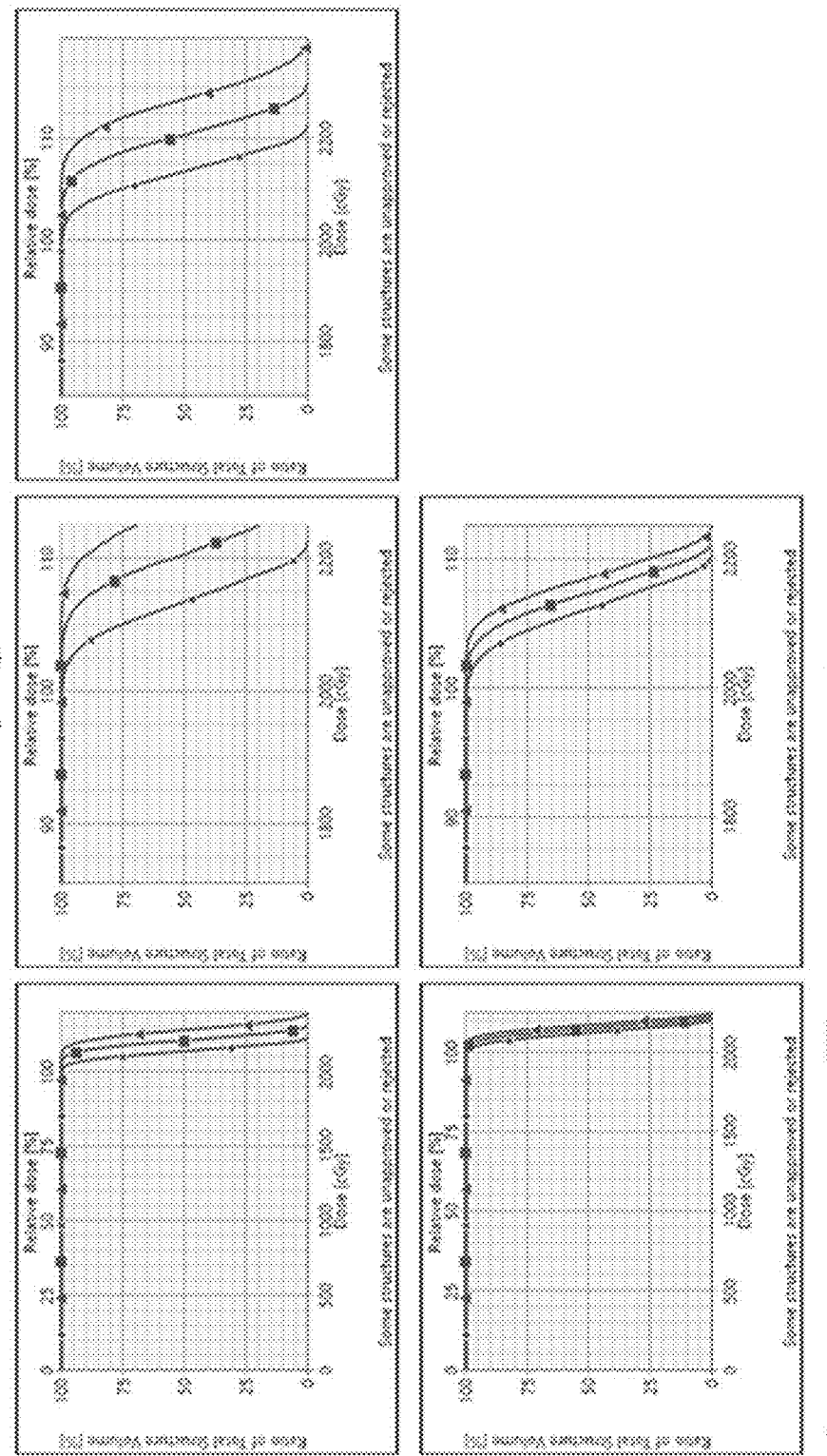
FIG. 6 is another graph of non-limiting example data comparing VMAT to a plan in accordance with one aspect of the present disclosure.

Referring to FIG. 6, graphs of the effect of DLG value on the DVH of a single VMAT and CAVMAT plan featuring four targets is shown. The combined PTVs at the three different DLG values are displayed. The VMAT DLG increases from 0.4 mm to 0.8 mm and 1.2 mm, the increased planned leaf gap causes an increased volume of tissue to be irradiated and shifts the DVH shoulder to a higher dose. Predictably, a larger shift is created when larger DLG values are used. The DVH of the CAVMAT plan at DLG values of 0.4, 0.8, and 1.2 mm is also displayed. CAVMAT also exhibits a shift in the combined PTV DVH, although the change is less drastic and the PTV is more effectively constrained to the prescription dose of 20 Gy.

For this example case and an increasing DLG, the VMAT plan demonstrated a sensitivity to changes in $V_{6Gy\ [cc]}$, $V_{12Gy\ [cc]}$, $V_{16Gy\ [cc]}$ of 33.2%/mm, 34.72%/mm, and 43.96%/mm, compared to 21.95%/mm, 22.33%/mm, and 26.11%/mm for the CAVMAT plan, respectively.

Similarly, the VMAT plan was found to be substantially more sensitive than CAVMAT to changes in the maximum, mean, and minimum dose applied to each target. For an increasing DLG, the VMAT plan demonstrated a sensitivity to changes in the target maximum, mean, and minimum dose of 8.33%/mm, 9.15%/mm, and 8.63%/mm, compared to a reduced sensitivity of 2.52%/mm, 4.23%/mm, and 3.0%/mm for CAVMAT.

For the non-limiting example group as a whole, with VMAT was more sensitive to changes in DLG. Considering all 10 plans, the VMAT plans demonstrated an average sensitivity to variation in $V_{6Gy\ [cc]}$, $V_{12Gy\ [cc]}$, $V_{16Gy\ [cc]}$ of 35.83±9.48%/mm, 34.12±6.61%/mm, and 39.22±8.41%/mm, respectively, compared to 23.18±4.53%/mm, 22.45±4.28%/mm, and 24.88±4.91%/mm for CAVMAT. Across the 46 targets, the VMAT plans demonstrated an average sensitivity to changes in target maximum, mean, and minimum dose of 9.08±3.45%/mm, 9.22±3.23%/mm, and 9.5±3.25%/mm, respectively, compared to an average of 3.2±1.63%/mm, 3.50±1.35%/mm, and 4.72±1.63%/mm, respectively. The VMAT plans exhibited a sensitivity of 8.93%/mm to increases in target coverage. In comparison, CAVMAT better restrained the target coverage to the prescription dose, with a sensitivity of 4.90%/mm.

The average limiting coverage ($D_{99\%[\%]}$) for all targets was evaluated at differing DLG values. The 10 VMAT and CAVMAT plans were evaluated using the MCS algorithm and a constant DLG value of 0.4 mm. The VMAT plans demonstrated an average MCS score of 0.036±0.019 with an average equivalent field size of 1.51±0.42 cm². The CAVMAT plans were less modulated, with an average MCS score of 0.052±0.031 with an average equivalent field size of 1.11±0.43 cm². The highly modulated MLC trajectories inherent to complex, conventional treatment plans, have been shown to reduce the dosimetric accuracy and effectiveness of a given plan. On average the CAVMAT plans produced a larger MCS score, correlating with a reduced plan complexity, compared to VMAT.

Log file analysis indicated of the 10 VMAT and CAVMAT plans following delivery that the average $V_{6Gy\ [cc]}$ increased by 0.93±1.43%, $V_{12Gy\ [cc]}$ increased by 0.90±1.38%, and $V_{16Gy\ [cc]}$ increased by 1.23±1.54%. In comparison, the log analysis of the CAVMAT plans indicated that the average $V_{6Gy\ [cc]}$ decreased by 0.035±0.14%, while $V_{12Gy\ [cc]}$ and $V_{16Gy\ [cc]}$ increased by 0.14±0.18% and 0.28±0.24%, respectively.

The post-delivery VMAT and CAVMAT plans exhibit a slightly increased average maximum, mean, and minimum target dose. The average maximum, mean, and minimum dose to each target increased by 0.53±0.46%, 0.52±0.46%, and 0.53±0.56% respectively. In comparison, the average maximum, mean, and minimum of the CAVMAT plans increased by 0.16±0.18%, 0.11±0.08%, and 0.07±0.11%, respectively. The average VMAT conformity index increased by 3.74±3.42%, from 1.48±0.21 to 1.54±0.24, compared to a CAVMAT change of 0.79±0.65%, from 1.38±0.19 to 1.39±0.19. The average target coverage of the VMAT plans changed minimally by 0.15±0.24% (99.50% to 99.65% coverage) following delivery, compared to a 0.01±0.28% (99.65% to 99.67% coverage) change for the CAVMAT plans.

In terms of MLC and gantry position error, the 10 VMAT and CAVMAT plans were comparable; substantial variation was not found in the MLC or gantry position error. The absolute average MLC positional error for the VMAT plans was 0.017±0.01 mm, compared to 0.023±0.02 mm for the CAVMAT plans. The MLC positional error for the CAVMAT plans was found to be small and comparable, demonstrating that the linear accelerator is capable of delivering CAVMAT plans effectively.

A gamma analysis of the 10 delivered plans revealed the average passing rate of the VMAT plans of 3%/1 mm criteria was 99.61±0.43%% compared to 99.98±0.06% for CAVMAT. When strict gamma analysis criteria was increased, the passing rate of the VMAT plans changed substantially. For a 2%/1 mm test criteria, the average VMAT passing rate was 98.54±1.29% compared to 99.98±0.06% for CAVMAT. Furthermore, for the strictest criteria of 1%/1 mm, the average VMAT gamma analysis passing rate was 94.53±4.42% compared to 99.28±1.74% for CAVMAT. For a dose difference criterion of 3%, the average passing rate of the VMAT plans was 96.03±4.44% compared to 99.17±0.74% for CAVMAT. By increasing dose difference criteria to 2%, the VMAT average passing criteria decreased to 91.74±5.89%, compared to 97.91±1.36% for CAVMAT. For the strictest criteria of 1% dose agreement, the average VMAT passing rate was further reduced to 74.78±13.00%, compared to a sustained 86.16±6.38% for CAVMAT. The gamma analysis demonstrated that the CAVMAT technique provided a greater overall agreement between planned and delivered dose than VMAT. The CAVMAT technique offered a superior gamma analysis passing rate for each gamma analysis criteria. The dose difference passing rate followed a similar trend, demonstrating that CAVMAT is capable of a greater dose agreement than VMAT, even with increasingly strict passing criteria.

The absolute average dose difference for the 16 VMAT and CAVMAT targets delivered to the SRS MapCHECK was evaluated for differing DLG values. All calculated isodose distributions were compared against a delivered 0.4 mm DLG baseline. For all calculated DLG of 0.4 mm and a 50% threshold, VMAT presented an absolute average dose difference of 1.46±0.72 cGy compared to 1.05±0.90 cGy (p=0.003). Similarly for a calculated DLG of 0.8 mm, the absolute average dose differences were 2.32±1.16 cGy and 1.94±1.35 (p=0.06) for VMAT and CAVMAT, respectively. Lastly, for a calculated DLG of 1.2 mm CAVMAT presented a reduced dose difference of 3.44±1.94 cGy compared to 5.52±1.61 cGy (p=7.7*10$^{-4}$).

Dose-volume thresholds are commonly used for SRS techniques to evaluate the potential for radiobiological complications. $V_{6Gy}$, $V_{12Gy}$, and $V_{16Gy}$ thresholds have been associated with radionecrosis and neurocognitive decline and are often used to assess the relative risk for SRS treatment plans. Sufficient modeling of dose-volume parameters in the treatment planning system may provide for the accurate determination of post-treatment complications. Lower dose values, like $V_{6Gy}$ and $V_{12Gy}$, lie in the penumbra region of the beam, where tissue exhibits a greater dose uncertainty. The clinical importance of these dose-volume parameters highlights the necessity for treatment planning techniques that are less sensitive to these uncertainties, such as provided with the systems and methods in accordance with the present disclosure.

If systematic error exists in the choice of DLG, or for cases where the optimal DLG varies between plans or between targets within a single plan, the dosimetric impact may be reduced by using a CAVMAT treatment planning technique in accordance with the present disclosure. A single isocenter radiotherapy of multiple targets method, such as CAVMAT, is more robust and less sensitive to DLG errors compared to a conventional VMAT technique. For cases when the value of the DLG was modified in the non-limiting examples, CAVMAT was more effective in maintaining the planned doses to healthy tissues as well as the coverage and dose applied to each target.

The present disclosure has described one or more preferred embodiments, and it should be appreciated that many equivalents, alternatives, variations, and modifications, aside from those expressly stated, are possible and within the scope of the invention.

The invention claimed is:

1. A method for controlling a radiation therapy system, the method comprising:
 a) assigning radiotherapy targets into a target subgroup for an arc geometry;
 b) generating a conformal arc based on the arc geometry to maximize blocking between the radiotherapy targets of the target subgroup for radiotherapy;
 c) determining an initial radiotherapy dose based upon the conformal arc;
 d) generating weighted conformal arcs by determining field weights to deliver a radiotherapy dose with a conformity to the radiotherapy targets;
 e) performing an inverse optimization process on the weighted conformal arcs to adjust the radiotherapy dose and the conformity of the target subgroup;
 f) determining a final dose for the radiotherapy targets, wherein determining the field weights includes minimizing the dose difference to the radiotherapy targets as represented by:

$$\Delta D = |D_{Rx} - \Sigma_f(d_{tf} \times W_f)|$$

where D represents dose to target t, $d_{tf}$ represents dose contribution to target t by field f, $D_{Rx}$ represents prescription dose, and $W_f$ represents weighting of field f.

2. The method of claim 1, further comprising assigning a plurality of radiotherapy targets to the target subgroup.

3. The method of claim 1, wherein the radiotherapy targets for the target subgroup are assigned by determining at least one of optimal collimator angles, target superposition, and effective depth of the radiotherapy targets.

4. The method of claim 3, wherein determining the collimator angle includes determining a collimator angle that can block between the radiotherapy targets in the target subgroup to prevent the radiotherapy targets from sharing a leaf pair of a multi-leaf collimator.

5. The method of claim 3, wherein the radiotherapy targets are assigned to the target subgroup to minimize target superposition as seen by a radiation beam by the radiation therapy system.

6. The method of claim 3, wherein the radiotherapy targets are assigned to the target subgroup such that discrepancies in target subgroup effective depth are minimized.

7. The method of claim 1, further comprising assigning a plurality of radiotherapy targets to a plurality of target subgroups.

8. The method of claim 1, wherein determining the field weights includes using a minimization routine, and wherein the minimization routine includes at least one of stochastic minimization, nonlinear minimization, or a Nelder-Mead multidimensional nonlinear minimizer.

9. The method of claim 1, further comprising delivering the determined final dose to the target subgroup to treat a condition of a subject.

10. A system for controlling a radiation therapy system, the system comprising:
 a computer system configured to:
 a) assign radiotherapy targets into a target subgroup for an arc geometry;
 b) generate a conformal arc based on the arc geometry to maximize blocking between the radiotherapy targets of the target subgroup for radiotherapy;
 c) determine an initial radiotherapy dose based upon the conformal arc;

d) generate weighted conformal arcs by determining field weights to deliver a radiotherapy dose with a conformity to the radiotherapy targets;

e) perform an inverse optimization process on the weighted conformal arcs to adjust the radiotherapy dose and the conformity of the target subgroup;

f) determine a final dose for the radiotherapy targets, and wherein the computer system is further configured to determine the field weights by minimizing the dose difference represented by:

$$\Delta D = |D_{Rx} - \Sigma_f (d_{tf} \times W_f)|$$

where D represents dose to target t, $d_{tf}$ represents dose contribution to target t by field f, $D_{Rx}$ represents prescription dose, and $W_f$ represents weighting of field f.

11. The system of claim 10, wherein the computer system is further configured to assign a plurality of radiotherapy targets to the target subgroup.

12. The system of claim 10, wherein the computer system is further configured to determine at least one of optimal collimator angles, target superposition, and effective depth of the radiotherapy targets.

13. The system of claim 12, wherein determining the collimator angle includes determining a collimator angle that can block between the radiotherapy targets in the target subgroup to prevent the radiotherapy targets from sharing a leaf pair of a multi-leaf collimator.

14. The system of claim 12, wherein the computer system is further configured to assign radiotherapy targets to the target subgroup to minimize target superposition as seen by a radiation beam by the radiation therapy system.

15. The system of claim 12, wherein the computer system is further configured to assign the radiotherapy targets to the target subgroup such that discrepancies in target subgroup effective depth are minimized.

16. The system of claim 10, wherein the computer system is further configured to determine the field weights by using a minimization routine, and wherein the minimization routine includes at least one of stochastic minimization, nonlinear minimization, or a Nelder-Mead multidimensional nonlinear minimizer.

17. The system of claim 10, further comprising a radiation source and an adjustable collimator, and wherein the computer system is further configured to control the radiation source to deliver the determined final dose to the first target subgroup to treat a condition of a subject by adjusting a configuration of the adjustable collimator.

18. A computer readable medium, comprising:

instructions stored on the computer readable medium for a) assigning a plurality of radiotherapy targets into a plurality of target subgroups for a plurality of arc geometries;

b) generating conformal arcs based on the arc geometries to maximize blocking between the plurality of radiotherapy targets of the plurality of target subgroups for radiotherapy;

c) determining initial radiotherapy doses based upon the conformal arcs;

d) generating weighted conformal arcs by determining field weights to deliver a radiotherapy dose with a conformity to the plurality of radiotherapy targets;

e) performing an inverse optimization process on the weighted conformal arcs to adjust the radiotherapy dose and the conformity of the plurality of target subgroups;

f) determining a final dose for the plurality of radiotherapy targets, and wherein determining the field weights includes minimizing the dose difference to the radiotherapy targets as represented by:

$$\Delta D = |D_{Rx} - \Sigma_f (d_{tf} \times W_f)|$$

where D represents dose to target t, $d_{tf}$ represents dose contribution to target t by field f, $D_{Rx}$ represents prescription dose, and $W_f$ represents weighting of field f.

* * * * *